United States Patent
Friedman (12)

(10) Patent No.: US 6,251,886 B1
(45) Date of Patent: Jun. 26, 2001

(54) METHODS OF USING TEMOZOLOMIDE IN THE TREATMENT OF CANCERS

(75) Inventor: Henry S. Friedman, Durham, NC (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/453,747

(22) Filed: Dec. 2, 1999

Related U.S. Application Data

(60) Provisional application No. 60/111,327, filed on Dec. 7, 1998.

(51) Int. Cl.$^7$ .................................................. A61K 31/33
(52) U.S. Cl. ................................................. 514/183
(58) Field of Search ............................................. 514/183

(56) References Cited

U.S. PATENT DOCUMENTS

| | | |
|---|---|---|
| 4,725,442 | 2/1988 | Haynes . |
| 5,091,187 | 2/1992 | Haynes . |
| 5,091,188 | 2/1992 | Haynes . |
| 5,260,291 | 11/1993 | Lunt et al. . |
| 5,731,304 | * 3/1998 | Baer et al. ............................ 514/183 |

FOREIGN PATENT DOCUMENTS

| | | |
|---|---|---|
| WO 90/11078 | 10/1990 | (WO) . |
| WO 94 15615 | 7/1994 | (WO) . |
| WO 98/07414 | 2/1998 | (WO) . |

OTHER PUBLICATIONS

Moore et al., Invest. New Drugs, 16(1), 77–79 Abstract Only, 1998.*
Grossman SA and Moynihan TJ., Neurol. Clin., 9:843–856, 1991.
Bleehen et al., Journal of Clinical Oncology, vol. 13, No. 4 (Apr.), 1995, pp 910–913.
O'Reilly et al., Eur. J. Cancer 1993; 29A:940.
Stevens et al., J. Med. Chem, 1984, 27, 196–201.
Wang et al., J. Chem., Soc., Chem. Commun., 1994, pp 1687–1688.
Friedman, et al. Cancer Research., 55: 2853–2857, 1995.
Bigner et al., Cancer Genet. Cytogenet., 18: 141–153, 1985.
Friedman, et al., J. Natl. Cancer Inst., 84: 1926–1931, 1992.
Kurpad et. al., Cancer Chemother. Pharmacol., 39: 307–365, 1997.
Olson, et. al., Arch. Neurol., 30: 122–137, 1974.
Theodore, et. al., Arch.Neurol., 38: 696–699, 1981.
Wasserstrom, et.al., Cancer, 49: 759–772, 1982.
Ongerboer de Visser, et. al., Neurology, 33: 1565–1572, 1983.
Horspool, et. al., J. Med. Chem., 33: 1393–1399, 1990.
Stevens, et. al., Cancer Res., 47: 5846–5852, 1987.
Newlands, et. al., Cancer Treat. Rep., 69: 801–805, 1985.
Newlands, et., al., Br.J. Cancer, 65: 287–291, 1992.
O'Reilly, et. al., Eur. J. Cancer, 29A:940–942, 1993.
Newton, et. al., Neurology, 40: 1743–1746, 1990.
Rodriguez, et.al., Cancer, 64: 2420–2423, 1989.
Green, et. al., Cancer Treat. Rep., 67: 121–132, 1983.
Kumar, et. al., Neurosurg., 40: 365–371, 1974.
Edwards, et. al., Cancer Treat. Rep., 64: 1179–1205, 1980.
Tsang, et. al., Cancer Chemother. Pharmacol., 27: 342–346, 1991.
Friedman, et. al., Cancer Res., 54: 4710–4714, 1994.
Friedman, et. al. Proc. Am. Assoc. Cancer Res., 34: 2691993. (Abstract).
Archer, Proc. Am. Assoc. Cancer Res., 37: 2981996. (Abstract).
Newlands, E. S. et al., XP–000921344, Cancer Treatment Reviews, "Temozolomide: A review of . . . ", vol. 23/1, pp. 35–61 (1997).
Archer G. E. et al., XP–000914793, Proceedings of the Amer. Assoc. for Cancer Research Annual Meeting, abstract, Regional delivery of . . . , vol. 40, pp. 296 (1999).
Plowman, Jacqueline et al., XP–000914803, Cancer Res., "Preclinical antitumor activity . . . ", vol. 54 (14), pp. 3793–99, (1994).
Database WPI, Derwent Publications Ltd., London, GB; AN 1998–189166, XP–002141134 JP 10 045589A (Schering Corp) (1998).
Bobola, Michael S. et al., XP–000914804, Clin. Cancer Res. "Role of 06–methylguanine–DNA . . . ", vol. 2(4), pp. 735–741 (1996).
Donelli, M. G., et al., XP–000921354, Cancer Chemotherapy and Pharmacology, "Do anticancer agents reach.....", vol. 30/4 pp. 251–260, (1992).

* cited by examiner

Primary Examiner—Jerome D. Goldberg
(74) Attorney, Agent, or Firm—James M. Gould; Allan N. Kutzenco

(57) ABSTRACT

Methods are disclosed for treating cancer in a patient in need of such treating comprising administering temozolomide in an amount effective to achieve a clinical response wherein the temozolomide is administered in a microcrystalline suspension.

18 Claims, 1 Drawing Sheet

METHODS OF USING TEMOZOLOMIDE IN THE TREATMENT OF CANCERS

This application claims benefit of provisional application No. 60/111,327 filed Dec. 7, 1998.

This invention was made with Government support under Grant Nos. NS30245, NS20023, and CA57725 from the National Institutes of Health. The Government has certain rights in this invention.

FIELD OF THE INVENTION

The present invention relates to methods of using microcrystalline compositions of temozolomide in the treatment of cancers, especially in the treatment of neoplastic meningitis and other cancers occurring in compartmentalized regions of the body such as the subarachnoid space.

BACKGROUND

First recognized in 1870 (Eberth, C. J., *Arch. Pathol. Anat. Physiol. Klin. Med.*, 49:51–63 (1870.), neoplastic meningitis is now being seen with increasing frequency, no doubt reflecting more effective therapy of systemic cancer as well as heightened awareness and improvements in diagnostic tools. Neoplastic meningitis can result from leptomeningeal dissemination of a spectrum of cancers, either arising from the central nervous system, such as medulloblastoma or high grade glioma, or resulting from invasion by lymphoma, leukemia, melanoma, sarcoma, or carcinoma (notably breast and lung carcinoma). Furthermore, the striking incidence in AIDS-related CNS lymphoma (which has a 50% incidence of leptomeningeal spread) suggests that an extensive population in the United States and abroad will require treatment of neoplastic meningitis. Unfortunately, current therapy of leptomeningeal disease is particularly ineffective with external beam radiotherapy and intrathecal chemotherapy, specifically methotrexate, thiotepa, or cytosine arabinoside only providing modest benefits, with mean survival following leptomeningeal tumor spread measured in months (Grossman S. A. and Moynihan T. J., *Neurol. Clin.*, 9:843–856, 1991 1991). Newer therapies are clearly needed for treatment of patients with cancer, especially patients with neoplastic meningitis and other cancers occurring in compartmentalized regions of the body.

SUMMARY OF THE INVENTION

The present invention provides methods of using microcrystalline compositions of temozolomide to treat cancer, especially neoplastic meningitis and other cancers occurring in compartmentalized regions of the body such as the subarachnoid space. In particular, the present invention provides a method for treating cancer in a patient in need of such treatment comprising administering temozolomide in an amount sufficient to achieve a clinical response, wherein the temozolomide is administered in a microcrystalline suspension.

Microcrystalline compositions in accordance with the present invention can be used to treat a variety of cancers in the human body, especially by means of regional temozolomide chemotherapy. In particular, methods are provided for treating tumors which can grow and metastisize within cavities of the human body, such as the peritoneum, central nervous system, the lungs, etc.

Microcrystalline compositions of temozolomide in accordance with the present invention can be administered by any number of means, including, e.g., intrathecally, intraventricularly, intraperitoneally, intrapleurally, intravenously, or by administration into an artery that supplies blood to a region of the body, e.g., intrahepatic artery administation to reach the liver, or delivery into the carotid artery system to reach the brain. In a preferred embodiment, microcrystalline suspensions of temozolomide can be administered intrathecally to the subarachnoid space, and the intrathecal administration can be intralumbar or intraventricular (via the Ommaya reservoir). Methods of delivering microcrystalline compositions of temozolomide intraarterially are also provided by the present invention, as are methods of administering such compositions directly into a tumor mass.

DETAILED DESCRIPTION

Figure 1:
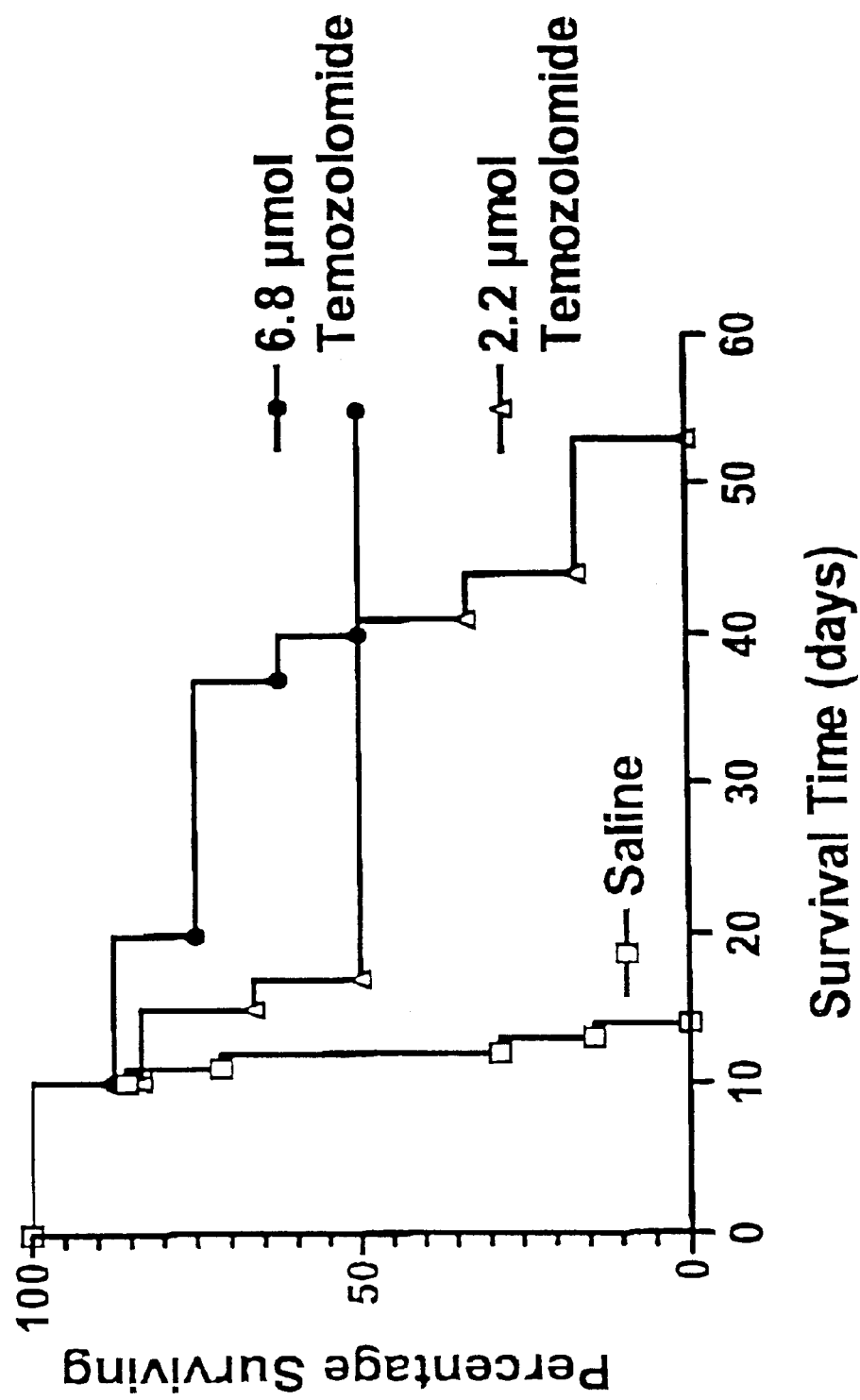
FIG. 1 is a graphical depiction showing percentage of surviving animals (athymic nude rats) over time in a study of intrathecal treatment of Mer– D54 MG human glioma xenograft neoplastic meningitis using a microcrystalline formulation of temozolomide. (Mer– D54 MG is DNA mismatch repair negative cell line). The dose schedule was 40 $\mu$L of temozolomide solution containing the amount of drug indicated twice per week for two weeks. Neoplastic meningitis was induced by injection of $5\times10^6$ cells into the subarachnoid space via an indwelling catheter. Treatment was initiated six days later. Median survival was increased >142% from 12.0 days in the group treated with saline to 29.0 days (p=0.0073) in the group treated with individual doses of 2.2 $\mu$mol of microcrystalline temozolomide and was increased >367% to >56 days (p=0.0015) in the group treated with individual doses of 6.8 $\mu$mol of microcrystalline temozolomide.

Temozolomide is an imidazole tetrazinone known for its anti-tumor effects. For example, in a Phase I study, clinical responses Were achieved in 17% of patients having advanced melanoma (Newlands E. S., et al. Br J Cancer 65 (2) 287–2981, 1992). In Phase II study, a clinical response was achieved in 21% of 60 patients with advanced melanoma (Journal of Clinical Oncology, Vol 13, No. 4 (April), 1995, pp 910–913). Treatment of gliomas in adults with temozolomide is also known (Eur. J. Cancer 1993; 29A:940). Treatment of the following cancers in adults with temozolomide has also been disclosed: metastatic melanoma; high grade glioma, glioblastoma and other brain cancers; lung cancer; breast cancer; testicular cancer; colon and rectal cancers; carcinomas; sarcomas; lymphomas; leukemias; and mycosis fungoides. For more information on temozolomide, reference can be made to, e.g., U.S. Pat. Nos. 5,260,291 and 5,731,304.

Temozolomide's mechanism of action is similar to dacarbazine, notably conversion to the methylating agent MTIC. However, unlike dacarbazine which requires metabolic dealkylation (a relatively inefficient process in humans compared to rodents) to form MTIC, temozolomide undergoes chemical conversion to MTIC under physiological conditions. The present inventor determined that the spontaneous conversion of this agent renders it an excellent candidate for regional therapy, including treatment of cancers such as neoplastic meningitis which occur in the subarachnoid space. However, it was also recognized that there were significant impediments to using temozolomide in such treatments, e.g., temozolomide is known to have poor solubility, and thus it was highly questionable whether one could prepare a temozolomide formulation that would be effective to achieve clinically effective concentrations within specific cavities of the body, and thereby effectively treat cancers that were compartmentalized in such cavities.

As described in more detail below, the present inventor found that by using microcrystalline compositions of temozolomide, cancers that were compartmentalized in body cavities or regions (e.g., subarachnoid spaces) could be successfully treated by achieving clinically effective concentrations of temozolomide in such cavities.

The term "temozolomide" is intended to mean a compound having the formula:

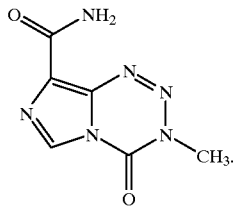

One chemical name for temozolomide is 3,4-dihydro-3-methyl-4-oxoimidazo-[5,1-d]-1,2,3,4-tetrazin-8-carboximide. Another chemical name is 8-carbamoyl-3-methylimidazo[5,1-d]-1,2,3,5-tatrazin-4(3H)-one). The synthesis of temozolomide is well known. See, for example, Stevens et al., *J. Med. Chem*, 1984, 27, 196–201 and Wang et al., *J. Chem. Soc., Chem. Commun.*, 1994, pp 1687–1688.

The microcrystalline formulations of temozolomide used in the following in vivo examples (set forth in the next section below) were prepared as follows:

Ingredients:

| | |
|---|---|
| 1,2-dilauroyl-sn-glycero-3-phosphocholine (DLPC) | 5 g |
| 1,2-dimyristoyl-sn-glycero-3-phosphocholine (DMPC) | 5 g |
| Temozolomide (TMZ) | 18 g |
| 25 mM sodium acetate buffer, pH 4 containing 5% (w/v) mannitol (TMZ Buffer) | 500 ml |

Preparation Steps:
1. Add 500 ml TMZ Buffer to a 1 liter beaker;
2. Add dry powdered phospholipid to the beaker and homogenize to wet the phospholipids;
3. Add dry powdered TMZ to the beaker and homogenize to wet the TMZ;
4. Pass through a M110 microfluidizer (e.g., a Model 110-EH Microfluidizer from Microfluidics, Inc.) two times at a pressure of approximately 14,000 psi.;
5. Fill vials;
6. Lyophilize and sterilize by gamma radiation.

The final constitution of the temozolomide suspension (active ingredient plus excipients) based on the above preparation method is estimated to be as follows:

33 mg/ml Temozolomide
25 mM Acetate Buffer
5 mg/ml DLPC
5 mg/ml DMPC
5 mg/ml Mannitol Additional microcrystalline suspensions of temozolomide can be prepared using methods known in the art. See, e.g., U.S. Pat. Nos. 5,091,188; 5,091,187; and 4,725,442; and International Patent Publication WO 98/07414; which are expressly incorporated herein by reference. For example, instead of using a microfluidizer, particle size reduction can be achieved, e.g., by homogenization, sonication, and other methods. With regard to the formulation itself, the phospholipid can be any natural or synthetic phospholipid, for example phosphatidylcholine, phosphatidylethanolamine, phosphatidylserine, phosphatidylinositol, phosphatidylglycerol, phosphatidic acid, lysophospholipids, egg or soybean phospholipid or a combination thereof. The phospholipid may be salted or desalted, hydrogenated or partially hydrogenated, or natural, semisynthetic, or synthetic. Other buffers can be used instead of sodium acetate, and in addition, surface modifiers such as non-ionic, anionic or cationic surfactants can also be added (see, e.g., International Patent Publication WO 98/07414).

EXAMPLES

A. Materials and Methods

Temozolomide Preparations—Standard formulation temozolomide (MW 194) was provided by Schering-Plough Research Institute (Kenilworth, N.J.). Saturated dosing solutions of this formulation were prepared by dissolving 3.1 mg/mL of the solid drug into sterile normal saline at room temperature and neutral pH followed by filter sterilization. The microcrystalline formulation of temozolomide was prepared as described in steps 1 through 9 set forth directly above. As indicated above, the process resulted in the following final constitution of the temozolomide suspension (active ingredient plus excipients, 2 ml/vial):

33 mg/ml Temozolomide
25 mM Acetate Buffer
5 mg/ml DLPC
5 mg/ml DMPC
5 mg/ml Mannitol Saturated dosing solutions of this formulation were then prepared by reconstituting 33 mg/mL of the sterile buffered microcrystalline drug with sterile water for injection at room temperature and neutral pH.

Xenografts—Well-characterized human malignant glioma (MG) xenografts maintained in our laboratory were used for all experiments. Tumors were excised and minced, then dissociated with 0.5% collagenase at room temperature in a trypsinazation flask for two hours. Viable cells were separated on a Ficoll density gradient, washed twice with Dulbecco's phosphate buffered saline, and resuspended. D-54 MG is the Duke University subline of A-172 established by (Giard et al., J. Natl. Cancer Inst., 51: 1417–1423, 1973). D-54-MG shows no $O^6$-alkyguanine-DNA alkyl-transferase (AGAT) activity and is considered Mer– (Friedman, et al. Cancer Research., 55: 2853–2857, 1995). D-456 MG was derived from a childhood glioblastoma multiforme as described previously (Bigner et al., Cancer Genet. Cytogenet., 18: 141–153, 1985; Friedman, et al., J. Natl. Cancer Inst., 84: 1926–1931, 1992). D456-MG has been shown to have measurable AGAT levels (17.7±3.6 μmol/mg protein) in prior studies and is considered Mer+ (Friedman et al., Cancer Research., 55: 2853–2857; 1995). D456 has also been shown to be resistant to 1,3-bis(2-chloroethyl)-1-nitrosourea (BCNU) (Kurpad et al., Cancer Chemother. Pharmacol., 39: 307–316, 1997).

Athymic Rat Model of NM—Subarachnoid catheters were implanted into female athymic rats (BIG:NIMR$^{mu}$ [SPF]) (190–240 g) as previously described (Fuchs, H. E. et. al., Cancer Res., 50: 1954–1959, 1990). These animals were maintained in the Duke University Cancer Center Isolation Facility according to institutional policy. Prior to catheter placement, the rats were anesthetized by an intraperitoneal injection of a mixture of ketamine (55 mg/mL)/ and xylazine (9 mg/mL) at a dose of 1 mL/kg. They were then placed in a stereotactic frame (David Kopf Instruments, Tujunga, Calif.) with their necks flexed at a 90° angle using a tilt adapter. A midline sagittal incision was made from the inion to the laminal arch of C1. The atlanto-occipital membrane was exposed and incised as was the underlying dura mater over the cisterna magna using the tip of a 20-gauge needle. A PE-10 catheter (Intramedic; Franklin Lakes, N.J.) with a 5-0 stainless steel wire stylet was then inserted into the subarachnoid space to the lumbar region (8.5 cm) by passing it along the posterior aspect of the spinal cord. The stylet was removed, a loose knot was tied in the catheter just above the opening of the dura mater, and the knot was secured in place with dental epoxy (Lang Dental Manufacturing Co., Chicago, Ill.). The exposed catheter end was then passed through the skin lateral to the incision. The incision was closed in 3 layers using 6-0 ethilon (Ethicon, Somerville, N.J.), and the catheter was temporarily occluded with a small piece of 2-0 stainless steel wire. The animals were allowed to recover for 7–10 days, and only rats showing normal weight, motor, and sensory function were used in these experiments.

Neoplastic meningitis (NM) was initiated by inoculation of tumor cells through the indwelling subarachnoid catheter. The animals were anesthetized by light halothane anesthesia, the 2-0 wire stylet was removed, and the appropriate number of dissociated cells (approximately $5 \times 10^6$) derived from the human MG xenografts described above were injected in a volume of 40 µL using a 1000 µL Hamilton syringe and injector. The catheter was then flushed with 20-µL of normal saline and was reoccluded with 2-0 wire. Treatment was initiated at a time corresponding to one third of the median survival time as estimated from past experiments with each xenograft in this model. Histologic evidence of tumor was confirmed in at least three animals at the time of treatment.

B. Toxicity and Efficacy Studies

For toxicity and efficacy studies, athymic rats were injected with 40 µL of temozolomide solution twice a week for two weeks. For the standard temozolomide formulation a saturated 16 mM solution was used such that each individual dose of 40 µL contained 0.64 µmol of drug resulting in an estimated maximal final cerebrospinal fluid (CSF) concentration (FCC) of 1.6 mM after each dose. For the microcrystalline formulation of temozolomide a 56 mM 110 mM, or saturated 170 mM solution was used such that each individual dose of 40 µL contained 2.2 µmol, 4.5 µmol, or 6.8 µmol of drug respectively. This resulted in estimated maximal FCCs of 5.6 mM, 11 mM, or 17 mM, respectively. Estimated FCC are based on the reported rat CSF volume in a rat of 400 µL (Meek et. at., Neuropharmacology, 12: 497–499, 1973).

Rat weight, neurological status, survival, and histological examination of the neuraxis were compared with a control group treated with normal saline for all experiments. Clinical neurological function included testing of the stepping and placing reflex and the ability to climb a 60° incline ramp. These functions have been reported to correlate with subarachnoid tumor growth in other animal models of NM (Kooistra, et al., Cancer Res., 46 317–323, 1986). Histologic examination was conducted on six representative cross-sections of the central nervous system (CNS) including forebrain at level of lateral ventricles, hindbrain at the level of the occipital lobe, and four equally spaced spinal sections including the cauda equina. These sections were evaluated microscopically for hemorrhage, necrosis, edema, demyelination, and arachnoid fibrosis. All experiments were performed in accordance with the Duke University Animal Use Committee approved protocol.

C. Statistical Analysis

Survival estimates and median survivals were determined using the method of Kaplan and Meier (Kaplan, et. al., J. Am. Statist. Assoc., 53: 457–481, 1958), and survival data was compared using the nonparametric logrank test.

D. Results

Lack of Efficacy of Standard Formulation Temozolomide Against Subarachnoid Human MG Xenografts Injection of 40 µL of a saturated solution of the standard formulation of temozolomide containing 0.64 µmol of drug into rats twice weekly for two weeks via indwelling subarachniod catheters produced no evidence of toxicity on clinical or histologic examination. Volumes >40 µL of any substance cannot be injected i.t. into rats in this model without producing deaths in control groups; therefore, this regimen of standard formulation of temozolomide was evaluated for efficacy.

Treatment of rats bearing subarachnoid D54-MG with this regimen beginning six days after implantation of $5 \times 10^6$ cells failed to increase median survival. Similarly, treatment of rats bearing subarachnoid D456-MG with the same regimen as described above beginning eight days after implantation of $5 \times 10^6$ cells increased median survival by 16.7% from 21.0 days to 24.5 days which was not statistically significant (p=0.5018).

Evaluation of Toxicity of Microcrystalline Formulation Temozolomide

To determine if the efficacy of intrathecal (i.t.) temozolomide could be enhanced by increasing its solubility, a microcrystalline preparation of temozolomide with greatly enhanced solubility was developed as described above. The increased solubility of this compound allowed up to 6.8 µmol of drug to be delivered with each 40 µL individual dose. The toxicity of this new preparation was evaluated in non-tumor bearing rats at individual doses of 6.8 µmol, 4.5 µmol, and 2.2 µmol given twice weekly for two weeks. One death was observed in nine rats (11%) treated at the highest temozolomide dose group, and no deaths or neurologic signs were evident in any of the other rats treated with temozolomide at the lower doses (Table 1).

TABLE 1

Toxicologic analysis of a multiple-dose regimen[a] of intrathecal microcrystalline temozolomide on athymic rats without tumors

| Dose of Microcrystalline Temozolomide Injected[a] | Estimated FCC[b] of Temozolomide | Survival | Neurologic Symptoms |
|---|---|---|---|
| 2.2 µmol | 5.6 mM | 8/8 | 0/8 |
| 4.5 µmol | 11 mM | 9/9 | 0/9 |
| 6.8 µmol | 17 mM | 8/9 | 0/9 |

[a]Doses indicated were given twice weekly for two weeks in 40 µL.
[b]FCC, final cerebrospinal fluid concentration.

Efficacy of Microcrystalline Formulation Temozolomide Against Subarachnoid Mer– D54-MG Human Xenograft To determine if the microcrystalline formulation of temozolomide would be efficacious against NM, athymic rats bearing established subarachnoid human MG xenografts were treated with this formulation as described above. Treatment of Mer– D54-MG human xenograft NM with this regimen beginning six days after implantation of $5 \times 10^6$ cells increased median survival by >142% from 12.0 days in the group treated with saline to 29.0 days (p=0.0073) in the group treated with 2.2 µmol of drug twice weekly for two weeks (FIG. 1). In the group receiving individual doses of 6.8 µmol, the median survival was increased by >367% to >56 days (p=0.0015) as compared to saline control. There was also a statistically significant dose-response relationship when there data were analyzed using the logrank test for linear trends (p=0.0013). All rats in the group treated with saline in this experiment died within 14 days. However, 4/8 rats treated with the highest dose of the microcrystalline temozolomide formulation survived >56 days and ¾ of the surviving rats had no clinical evidence of neurologic symptoms or histologic evidence of tumor.

Treatment with microcrystalline temozolomide at either dose level produced minimal toxicity in this experiment (Table 2). As expected, all rats that died developed progressive neurologic symptoms. In the group of rats treated with low dose temozolomide, ⅚ animals had histological evidence of tumor while one animal died early in the experiment secondary to ventriculitis and meningitis. No evidence of hemorrhage, necrosis, or arachnoid fibrosis was identified in any rat in any group. Small focal areas of demyelination in a patchy distribution, located in the long tracks of the spinal cord, but not involving greater than 5% of visible spinal cord tracks, were identified in ⅜ rats of the group treated with the highest dose of microcrystalline temozolomide. However, none of the rats in the groups treated with the lower doses of microcrystalline temozolomide or with saline had any evidence of demyelination.

Theodore, et. al., Arch. Neurol., 38: 696–699, 1981; Wasserstrom, et. al., Cancer, 49: 759–772, 1982; Ongerboer de Visser, et. al., Neurology, 33: 1565–1572, 1983; Grossman, et al., Neurol. Clin., 9: 843–856, 1991). The deficiencies of current therapeutic interventions underlie the rapid death of patients following the diagnosis of leptomeningeal tumor spread. (In particular, given the rapid time to progression and the aggressive nature of this stage of the disease, there has been limited success with treatment options such as external beam radiation therapy and previous chemotherapeutic treatments).

Temozolomide, the 3-methyl derivative of mitozolomide, is a second generation imidazo-tetrazinone with activity against a spectrum of murine tumors (Horspool, et. al., J. Med. Chem., 33: 1393–1399, 1990; Friedman, et. al., Cancer Res., 55: 2853–2857, 1995; Stevens, et. al., Cancer Res., 47: 5846–5852, 1987). Despite severe and unpredictable thrombocytopenia observed with mitozolomide in clinical trials (Newlands, et. al., Cancer Treat. Rep., 69: 801–805, 1985), temozolomide was advanced to clinical trial, in part due to the observation of its spontaneous chemical conversion to MTIC without the need for metabolic activation. Initial Phase I trials of single-dose i.v. and, subsequently, oral temozolomide demonstrated dose-limiting myelosuppression and trivial antineoplastic activity. However, Phase I and

TABLE 2

Histopathologic effects of a multiple-dose regimen[a] of intrathecal microcrystalline temozolomide on athymic rats with Mer- D54-MG human glioma xenograft neoplastic meningitis

| Dose of Microcrystalline Temozolomide Injected | Estimated FCC[b] of Temozolomide | Survival at 180 days | Neurologic Symptoms | Histologic Evidence of Tumor | Hemorrhage | Necrosis | Demyelination[d] | Arachnoid Fibrosis |
|---|---|---|---|---|---|---|---|---|
| Normal Saline | 0 mM | 0/7 | 7/7 | 7/7 | 0/7 | 0/7 | 0/7 | 0/7 |
| 2.2 μmol | 5.6 mM | 0/6 | 6/6 | 5/6[c] | 0/6 | 0/6 | 0/6 | 0/6 |
| 6.8 μmol | 17 mM | 4/8 | 5/8 | 5/8 | 0/8 | 0/8 | 3/8 | 0/8 |

[a]Doses indicated were given twice weekly for two weeks in 40 μL.
[b]FCC, final cerebrospinal fluid concentration.
[c]One animal died secondary to ventriculitis and meningitis early in the experiment.
[d]Small focal areas of demyelination in a patchy distribution located in the long tracts of the spinal cord but not involving >5% of visible fibers.

Efficacy of Microcrystalline Formulation Temozolomide Against Mer+ D456-MG Human Xenograft Treatment of rats bearing subarachnoid, BCNU-resistant human glioma xenograft D456-MG with microcrystalline temozolomide using the regimen described above beginning eight days after implantation of $5\times10^6$ cells increased median survival by >131% from 26.0 days in the control group treated with saline to >60 days at all individual doses tested ranging from 2.2 μmol to 6.8 μmol (p<0.0058). There was also a statistically significant dose-response relationship when these data were analyzed using the logrank test for linear trends (p=0.0002). In the rats treated with microcrystalline temozolomide at the low (2.2 μmol) and intermediate (4.5 μmol) doses, ⅝ and 9/10 rats respectively survived >60 days and all survivors had no clinical evidence of neurologic symptoms or histologic evidence of tumor. In the group treated with the highest temozolomide dose (6.8 μmol), ⅝ survived and all survivors had no clinical evidence of neurologic symptoms or histologic evidence of tumor.

E. Discussion of Results

Neoplastic meningitis (NM) represents a lethal final common pathway for a spectrum of malignancies originating in the CNS or in extraneural sites that commonly metastasize to the CNS (Olson, et. al., Arch. Neurol., 30: 122–137, 1974;

II trials that used a five-day regimen revealed dose-limiting myelosuppression but intriguing anti-neoplastic activity, including responses in patients with high-grade glioma (Newlands, et. al., Br. J. Cancer, 65: 287–291, 1992; O'Reilly, et. al., Eur. J. Cancer, 29A: 940–942, 1993). Previous clinical trials have supported the activity of other methylating agents against brain tumors including procarbazine with results comparable to adjuvant BCNU (Newton, et. al., Neurology, 40: 1743–1746, 1990; Rodriguez, et. al., Cancer, 64: 2420–2423, 1989; Green, et. al., Cancer Treat. Rep., 67: 121–132, 1983; Kumar, et al., Neurosurg., 40: 365–371, 1974; Edwards, et. al., Cancer Treat. Rep., 64: 1179–1205, 1980). However, no other methylating agents have undergone extensive evaluation in clinical trials for patients with CNS tumors, although streptozotocin was evaluated in a brain tumor study group trial. Specifically, no methylating agents are currently available for intrathecal (i.t.) use.

The attraction to the oncologist of regional therapy of NM is the potential for achieving very high drug concentrations in the subarachnoid space while minimizing systemic exposure and hence toxicity. The dose-limiting stem cell toxicity produced by temozolomide has limited the use of this agent although stem cell reconstitution does broaden its applications. Intrathecal delivery in the model described in this report provided a maximal estimated FCC of temozolomide of 3,300 mg/L after only a single dose. This compares favorably with peak serum concentrations after oral therapy of only approximately 10 mg/L (Newlands, et al., Br. J. Cancer, 65: 287–291, 1992). In addition, based on CSF to plasma ratios for the area under the plasma concentration time curve from zero to infinity, penetration of systemic temozolomide into the CSF ranges from 41% to 44% in the rat and 29.8% in Rhesus monkeys. Thus, i.t. delivery of microcrystalline temozolomide could potentially provide a >750-fold drug delivery advantage with minimal systemic toxicity.

The recent generation of a panel of xenografts derived from childhood and adult high-grade gliomas (Giard, et. al., J. Natl. Cancer Inst., 51: 1417–1423, 1973; Friedman, et. al., Cancer Research., 55: 2853–2857; 1995; Bigner, et al., Cancer Genet. Cytogenet., 18: 141–153, 1985), and the development of an athymic rat model of NM (Fuchs, et. al., Cancer Res., 50: 1954–1959, 1990), provided the opportunity for preclinical definition of the activity of novel anti-neoplastics against tumors commonly progressing to NM. Previous studies demonstrated the activity of temozolomide against a series of human CNS xenografts growing subcutaneously in athymic nude mice (Friedman, et. al., Cancer Research., 55: 2853–2857, 1995) and provided the rationale for development of an i.t. approach. The marked insolubility of temozolomide, however, has previously precluded regional use of this methylating alkylator.

In contrast to standard temozolomide formulations, microcrystalline formulations of temozolomide were found to have enhanced solubility. The data presented provide evidence supporting the efficacy of this novel preparation of temozolomide for use i.t. against NM. Although only minimal efficacy was obtained using the standard formulation of temozolomide, the enhanced solubility of the microcrystalline formulation, by allowing increased drug delivery, produced substantial anti-neoplastic activity. In the experiments reported here, this enhancement in drug delivery provided a significant increase in median survival when used to treat a BCNU-sensitive, Mer– human MG xenograft growing in the subarachnoid space of athymic rats at all temozolomide doses tested. Intrathaecal microcrystalline temozolomide was also effective against a BCNU-resistant, Mer+ human MG xenograft in the same model. This suggests that i.t. microcrystalline temozolomide may be active against a spectrum of malignancies metastatic to the subarachnoid space. As a methylating agent, temozolomide has a unique mechanism of action among chemotherapeutic agents approved for i.t. use. This may be particularly useful against NM secondary to glial neoplasms because of the high incidence of alkylator drug resistance found with such neoplasms.

The activity of i.t. microcrystalline temozolomide was seen without significant systemic or CNS toxicity. In non-tumor-bearing animals only one death in nine rats was observed at the highest deliverable dose, and the remainder of the rats exposed to microcrystalline temozolomide demonstrated no weight loss or neurologic symptoms. Although there was no correlation with clinical symptoms or signs, three out of eight rats in the high dose group did demonstrate some evidence of patchy demyelination involving less than 5% of the spinal cord long tracks. Thus, the highest dose of microcrystalline temozolomide used in the present experiments could be considered toxic. This would warrant calculating a starting dose for humans based on the 4.5 $\mu$mol dose also shown to have efficacy in the present model. Given that the measured CSF space in humans, which ranges from 90 to 200 mL (Snyder, et. al., Oxford: Pergamon Press, Report of the Task Group on Reference Man. p 219, 1986), is >225-fold larger than the estimated 400 $\mu$L CSF space in rats (Meek, et. al., Neuropharmacology, 12: 497–499, 1973), a reasonable estimate of a potentially maximum tolerated dose for humans might be four doses over two weeks of 1000 $\mu$mol microcrystalline temozolomide each in 9 mL. Therefore 10% of this dose, four doses of 100 $\mu$mol microcrystalline temozolomide over two weeks, would be a reasonable suggested starting dose for a dose escalation study. This would provide an estimated maximal FCC after each individual dose of between 0.5 mM and 1.1 mM. Based on preclinical data, temozolomide is effective in vitro at 0.1 mM (Tsang, et. al., Cancer Chemother. Pharmacol., 27: 342–346, 1991), and therapeutic concentrations in the brain after systemic administration peak at between 0.041 mmol/Kg and 0.056 mmol/Kg. Therefore, even at the proposed starting doses, i.t. microcrystalline temozolomide might be expected to demonstrate efficacy.

These studies suggest that i.t. temozolomide warrants evaluation in patients with NM. Similar clinical results with i.t. melphalan (Friedman, et. al., Cancer Res. 54: 4710–4714, 1994) led to a current Phase I trial of melphalan and activity has been seen in patients with leptomeningeal medulloblastoma and pineoblastoma. A novel microcrystalline preparation of Busulfan that demonstrated efficacy in this NM model is now being evaluated in a Phase I clinical trial as well (Friedman, et. al., Proc. Am. Assoc. Cancer Res., 34: 269 1993. (Abstract); Archer, Proc. Am. Assoc. Cancer Res., 37: 298 1996. (Abstract)

MORE DETAILED DISCUSSION OF TREATMENT REGIMENS

A broad spectrum of human cancers can be effectively treated by the methods of the present invention. These include but are not limited to neoplastic meningitis occurring in the subarachnoid space. Neoplastic meningitis can arise from several sources, including, e.g., (a) from a primary brain tumor (e.g., medulloblastomas, gliomas (including high grade glioma), or glioblastoma), or other central nervous system tumor, (b) from a primitive neuro-ectodermal tumor, or (c) from an extraneural malignancy such as a melanoma, carcinoma (e.g., breast carcinoma, lung carcinoma), sarcoma, lymphoma, leukemia, germ-cell tumor, or mycosis fungoides.

For example, with regard to medulloblastoma, the most common primary central nervous system malignancy in childhood, this cancer is a highly aggressive neoplasm with a marked predilection for leptomeningeal dissemination. Although therapeutic intervention for such dissemination in this tumor is often unsuccessful, the methods of the present invention can be useful to positively impact efficacy parameters in the respective patient populations with tumor seeds in the CSF. It is possible and expected that the overall survival may be prolonged, that the time of tumor progression may be delayed and that patients may benefit from a delayed onset of symptoms, in particular of symptoms related and arising from tumor growth at the subarachnoid space.

With regard to carcinomas, methods of the present invention can be used to treat neoplastic meningitis arising from solid tumors such as, e.g., breast carcinoma, colorectal carcinoma, or head and neck carcinoma.

Other important embodiments of treatments provided by the present invention include treatment of neoplastic meningitis arising from CNS lymphoma (especially AIDS-related CNS lymphoma), as well as neoplastic meningitis arising from melanoma.

This invention contemplates treating the aforementioned cancers and other cancers at various stages of the disease. In particular, the aforementioned cancers and others can be treated at stages where these cancers have caused tumor metastases in particular compartments (as referred to previously), e.g., in the subarachnoid space. Such conditions, namely metastatic growth in these body compartments, may arise at any time from the initial diagnosis up to and including the terminal stage of such cancers; more frequently these conditions occur in later, advanced stages of the respective cancer.

A person suffering from cancer may exhibit one or more of clinical findings/symptoms, including but not limited to, the following: physical presence of a cancerous tumor, pain, fatigue, weight loss, impaired organ function (related to the involved anatomical area), anemia (and other laboratory abnormalities), bleeding, para-neoplastic symptoms and/or neurological symptoms (in particular in patients with primary brain tumors, brain metastases or tumor spread to the meningies or the subarachnoid space).

To practice the invention, temozolomide is administered to the patient exhibiting one of more of the above clinical findings or symptoms in an amount effective to eliminate or at least alleviate one or more of the clinical findings or symptoms. Thus, as used herein, the terms "effective amount" or "amount effective to achieve a clinical response" a refer to the amount or concentration of temozolomide sufficient to eliminate or at least alleviate one or more of the aforementioned clinical findings or symptoms associated with or resulting from the respective malignancy at the respective stage. (It should be understood that the meaning of the terms "effective amount" or "amount effective to achieve a clinical response" can be with reference to any one (or more) of various outcome parameters, e.g., achievement of a particular clinical response, prolongation of overall survival, time to progression, and/or time to onset of symptoms).

In preferred embodiments of the present invention, administration of microcrystalline suspensions of temozolomide can be by any means which causes a localized, regional effect. For example, the drug may be administered intrathecally (e.g., intralumbar or intraventricular via the Ommaya reservoir), intraventricularly, intraperitoneally (e.g., to treat ovarian cancer), intrapleurally, directly into a tumor mass, into a tumor lesion, or into the arterial blood supply to a tumor. Preferred examples of treating tumors by administration into a blood supply for those tumors include perfusion into the carotid artery system (e.g., to treat head and neck cancer and/or primary brain tumors such as gliomas), limb perfusion, or intrahepatic artery administration.

As is readily apparent to those of skill in the art, maximum concentrations are desirable for their cytotoxic effects on the tumor cells; however these concentrations should not cause toxic side effects to other portions of the treated individual. Precise doses and regimens can be empirically determined by those of skill in the art depending upon the particular condition of the patient and the tumor involved.

Specific dosing regimens may vary depending on the route of administration. For example, while preferred doses of microcrystalline temozolomide for intrathecal administration are from 0.1 to 100 mg, doses are more preferably from 0.5 to 20 mg. Preferably, a final temozolomide concentration of 100 $\mu$M to 25 mM, more preferably 250 $\mu$M to 5 mM, is achieved in the cerebrospinal fluid (CSF). A preferred dosing schedule for intrathecal administration is only once a day, but can include more frequent dosing. For example, on day 1, a dose of 0.5 to 10 mg can be administered as an initial dose, and 24 hours later another dose can be administered. Then, for example, treatments can be administered twice a week for two weeks in a row, then once a week for two consecutive weeks, followed by once a week every other week for two treatments, then one treatment per month thereafter.

With regard to intratumoral administration, doses of microcrystalline temozolomide are preferably from 0.5 to 50 mg per $m^2$. Doses for administration by arterial perfusion (such as perfusion into the carotid artery system to treat gliomas) are preferably from 1 to 200 mg per $m^2$, but more preferably from 5 to 200 mg per $m^2$.

Regardless of the total amount of the dosage or the length of the administration period, it may be preferable to administer a larger bolus dose for the first dose to achieve a better depletion of the DNA alkyltransferase, followed by a maintenance dose to maintain the depletion.

In general, treatment cycles may be continued until a disease progression or until intolerable side effects are encountered. The dosage may be decreased, if intolerable side effects or hematologic toxicity are encountered.

The following response criteria may be used, e.g., in cases of neoplastic meningitis:

Complete responses (CR): Two consectutive negative CSF cytologic examinations and total disappearance of radiographically discernable extramedullary intradural tumor. If no radiographically identifiable tumors were present at a study entry, there must be three consecutive negative cytologic examinations. For patients treated by the intraventricular route, there must be at least one negative lumbar spinal fluid sample obtained concurrently with the last (i.e. after treatment #4) negative ventricular CSF sample.

Partial response (PR): Greater than 50% reduction in tumor size as measured by the sum of the largest perpendicular diameters of the measurable lesion or two consectutive negative cytology's with <50% reduction in tumor size (if the initial cytology was positive).

Stable disease (SD): Either negative or positive CSF cytology, <50% reduction in tumor size and no clinical progression.

Progressive disease (PD): Conversion of previously negative cytology to positive, >25% increase in the size of measurable timor, appearance of a new radiographically demonstrable extramedullary intradural lesion, of SD with evidence oa neurologic deterioration due to tumor progression.

In monitoring administration of temozolomide for toxicity and efficacy, any observed neurological changes (including any underlying neuro-anatomical/pathophysiological changes) are measured and monitored. For example, functional neurological loss, numbness paralysis, or pain may be observed and should be minimized.

A common, but tolerable side effect of both temozolomide is nausea and vomiting. This can be alleviated by administering an anti-emetic in conjunction with the temozolomide. An anti-emetic 5-HT3 antagonist, or Ondansetron (p.o. in a dose of about 8 mg about 30 minutes), can be given before temozolomide administration. Of course other anti-emetics such as Hasaldol, Benadryl, and Ativan may also be used as needed.

With regard to combination treatment, the microcrystalline compositions of temozolomide may be administered alone or in combination with other chemotherapeutic agents, including but not limited to, e.g., cyclophosphamide or irinotecan. The temozolomide compositions can also be administered with a DNA alkyltransferase (ATase) inhibitor such as $O^6$ benzyl guanine.

The following examples serve to illustrate, but not limit dosing according to the invention.

EXAMPLES OF PROPOSED HUMAN TREATMENT REGIMENS

Set forth below are specific examples of proposals for preferred treatment regimens for intrathecal Temozolomide administered via intralumbar or intraventricular routes. In these regimens, each dose is repeated on a twice a week basis (i.e., q 3–4 days) for a total of 4 doses. The same route of administration is used throughout each specific treatment regimen.

Administration

Intralumbar Administration: LP

For patients receiving temozolomide via the intralumbar route, the drug should preferably be administered in a final total volume of 10 cc in preservative-free 0.9% sodium chloride for injection, USP. Drug administration should be isovolumetric: i.e., an amount of CSF equivalent to that to be administered must be removed prior to drug injection. Following intralumbar injection, patients should lie supine either in the flat or Trendelenburg position for approximately 30 minutes.

Intraventricular Administration: Ommaya Reservoir

After appropriate sterile preparation of the reservoir site, the drug should preferably be administered into the Ommaya reservoir via a 23 gauge (or smaller) scalp vein needle in a final total volume of 10 cc in preservative-free 0.9% sodium chloride for injection, USP. Drug administration should be isovolumetric; i.e. an amount of CSF equivalent to that to be administered must be removed from the reservoir prior to drug injection. The drug should be injected slowly at a rate not exceeding 2 ml/min. Following administration of the drug, the reservoir should be flushed slowly for 1 to 2 minutes with approximately 2 cc of either CSF (removed prior to drug injection) or 0.9% saline. After the flush injection, the reservoir should be pumped 4 to 6 times.

Unless there is surgical or clinical contraindication, patients will be treated via intraventricular administration (Ommaya reservoir).

Starting Dose: For adults (age >18 years), The starting dose of temozolomide under this particular regimen is preferably from 0.5 mg to 6 mg, more preferably 1 mg.

Criteria for Subsequent Treatment:

If ANC is $\geq 1500/mm^3$ and platelet count is $\geq 100,000/mm^3$ (absent use of growth factors to enhance levels), then repeat doses may be administered otherwise additional temozolomide is delayed. If subsequent administrations cannot be administered on the scheduled day of dosing, the CBC can be repeated weekly for up to and including 3 weeks until the ANC is >$1500/mm^3$ and platelet count >$100,000/mm^3$. If these hematological criteria are met, temozolomide may be administered.

Modifications and variations of this invention will be apparent to those skilled in the art. The specific embodiments described herein are offered by way of example only, and the invention is not to be construed as limited thereby.

All publications, patents and patent applications cited herein are incorporated in their entirety by reference to the same extent as if each individual publication, patent or patent application was specifically and individually indicated to be incorporated by reference.

What is claimed is:

1. A method of treating a neoplastic meningitis cancer sensitive to cytotoxic effects of temozolomide in a patient in need of such treatment, comprising administering to the patient an effective amount of a microcrystalline suspension of temozolomide which has an enhanced solubility compared to a non-microcrystalline form of temozolomide.

2. The method of claim 1, wherein the microcrystalline suspension of temozolomide is administered intrathecally to a subarachnoid space or cavity inside of the patient.

3. The method of claim 2, wherein from 0.1 to 100 mg of temozolomide is administered to the patient.

4. The method of claim 1, wherein the neoplastic meningitis cancer arises from a central nervous system tumor, a primitive neuroectodermal tumor or an extraneural malignancy.

5. The method of claim 4, wherein the extraneural malignancy is a melanoma, carcinoma, sarcoma, lymphoma, leukemia, germ-cell tumor or mycosis fungoide.

6. The mood of claim 5, wherein the carcinoma is a breast, lung, colorectal, head or neck carcinoma.

7. The method of claim 4, wherein the central nervous system tumor is a primary brain tumor or a lymphoma.

8. The method of claim 7, wherein the primary brain tumor is a medulloblastoma, glioma or glioblastoma.

9. The method of claim 1, wherein the neoplastic meningitis arises from a malignant melanoma.

10. The method of claim 1, wherein the microcrystalline suspension of temozolomide is administered intrathecally, intraventricularly, intraheperitoneally, intrapleurally, intraarterially or directly into a tumor mass or lesion.

11. The method of claim 10, wherein the intraarterial administration is carried out by perfusion into a cartoid or intrahepatic artery.

12. The method of claim 11, wherein the intrarterial perfusion of temozolomide is administered in an amount of from 1 to 200 mg per $m^2$ of a body surface area of the patient.

13. A method of treating a cancerous tumor sensitive to cytotoxic effects of temozolomide in a patient in need of such treatment, comprising administering to a region containing the cancerous tumor in the patient an effective amount of a microcrystalline suspension of temozolomide which has an enhanced solubility compared to a non-microcrystalline form of temozolomide.

14. The method of claim 13, wherein from 0.1 to 100 mg of temozolomide is administered to the patient.

15. The method of claim 13, wherein the cancerous tumor is a neoplastic meningitis tumor.

16. The method of claim 15, wherein the neoplastic meningitis tumor arises from a central nervous system tumor, a primitive neuroectodermal tumor or an extraneural malignant tumor.

17. The method of claim 16, wherein the extraneural malignant tumor is a melanoma, carcinoma, sarcoma, lymphoma, leukemia, germ-cell or mycosis fungoide tumor.

18. The method of claim 13, wherein the microcrystalline suspension of temozolomide is administered directly into a mass or lesion of the tumor.

* * * * *